(12) United States Patent
Truscott et al.

(10) Patent No.: US 11,966,824 B2
(45) Date of Patent: Apr. 23, 2024

(54) IDENTIFICATION AND VERIFICATION OF MEDICATION

(71) Applicant: Accenture Global Solutions Limited, Dublin (IE)

(72) Inventors: Andrew J. Truscott, Spring, TX (US); Ethan R. Bischoff, St. Paul, MN (US)

(73) Assignee: Accenture Global Solutions Limited, Dublin (IE)

( * ) Notice: Subject to any disclaimer, the term of this patent is extended or adjusted under 35 U.S.C. 154(b) by 738 days.

(21) Appl. No.: 17/117,919

(22) Filed: Dec. 10, 2020

(65) Prior Publication Data

US 2021/0098104 A1    Apr. 1, 2021

Related U.S. Application Data

(60) Continuation-in-part of application No. 16/718,519, filed on Dec. 18, 2019, now Pat. No. 11,682,478, (Continued)

(51) Int. Cl.
*G16H 20/10* (2018.01)
*G06N 20/00* (2019.01)
(Continued)

(52) U.S. Cl.
CPC ........... *G06N 20/00* (2019.01); *G06T 7/0002* (2013.01); *G06V 10/147* (2022.01);
(Continued)

(58) Field of Classification Search
CPC .......... G06N 20/00; G06N 3/045; G06N 3/08; G06T 7/0002; G06V 10/147;
(Continued)

(56) References Cited

U.S. PATENT DOCUMENTS 5,597,995 A    1/1997  Williams et al.
7,028,723 B1   4/2006  Alouani et al.
(Continued)

FOREIGN PATENT DOCUMENTS

| EP | 3340193 A1 | 6/2018 |
| WO | 2011108965 A1 | 9/2011 |
| WO | 2020027923 A1 | 2/2020 |

OTHER PUBLICATIONS

Extended European Search Report for Application No. EP21196869, dated Jun. 7, 2022, 10 pages.

*Primary Examiner* — Maroun P Kanaan
(74) *Attorney, Agent, or Firm* — Harrity & Harrity, LLP

(57) ABSTRACT

In some implementations, a device may receive prescription information associated with a medication in a container. The device may cause a camera to capture first image data associated with the medication while the medication is in the container and the container is positioned on a receptacle. The device may cause an adjusting device to reposition the container on the receptacle. The device may cause the camera to capture second image data associated with the medication while the medication is in the container. The device may process, via a neural network, the first image data and the second image data to identify the medication based on depictions of individual units of the medication included in the first image data and the second image data. The device may verify the medication based on the prescription information and an identifier of the medication provided by the neural network.

20 Claims, 7 Drawing Sheets

Related U.S. Application Data which is a division of application No. 16/276,059, filed on Feb. 14, 2019, now Pat. No. 10,593,425.

(60) Provisional application No. 63/092,735, filed on Oct. 16, 2020, provisional application No. 62/769,132, filed on Nov. 19, 2018.

(51) Int. Cl.

| | | |
|---|---|---|
| *G06T 7/00* | (2017.01) | |
| *G06V 10/147* | (2022.01) | |
| *G06V 10/764* | (2022.01) | |
| *G06V 10/776* | (2022.01) | |
| *G06V 10/82* | (2022.01) | |
| *G06V 20/66* | (2022.01) | |
| *G16H 10/60* | (2018.01) | |
| *G16H 20/13* | (2018.01) | |
| *G16H 50/20* | (2018.01) | |

(52) U.S. Cl.
CPC .......... *G06V 10/764* (2022.01); *G06V 10/776* (2022.01); *G06V 10/82* (2022.01); *G06V 20/66* (2022.01); *G16H 10/60* (2018.01); *G16H 20/13* (2018.01)

(58) Field of Classification Search
CPC .... G06V 10/764; G06V 10/776; G06V 10/82; G06V 20/66; G16H 10/60; G16H 20/13; G16H 40/20; G16H 40/63; G16H 50/20
See application file for complete search history.

(56) References Cited

U.S. PATENT DOCUMENTS

| | | |
|---|---|---|
| 8,060,249 B2 | 11/2011 | Bear et al. |
| 8,345,989 B1 | 1/2013 | Bresolin et al. |
| 8,930,207 B2 | 1/2015 | Keravich et al. |
| 9,251,493 B2 | 2/2016 | Jacobs et al. |
| 9,679,114 B2 | 6/2017 | Iantorno et al. |
| 9,721,418 B2 | 8/2017 | van Ooyen et al. |
| 9,770,389 B2 | 9/2017 | Koike et al. |
| 10,073,954 B2 | 9/2018 | Chen et al. |
| 10,593,425 B1 | 3/2020 | Truscott et al. |
| 2006/0041330 A1 | 2/2006 | Ansari et al. |
| 2008/0086326 A1 | 4/2008 | Moura et al. |
| 2009/0012818 A1 | 1/2009 | Rodgers |
| 2010/0018941 A1 | 1/2010 | Kerr et al. |
| 2010/0131097 A1 | 5/2010 | Young et al. |
| 2013/0092700 A1 | 4/2013 | Braunstein |
| 2015/0227719 A1* | 8/2015 | Ranalletta ................ A61J 3/00 141/83 |
| 2018/0089394 A1 | 3/2018 | Hyde et al. |
| 2018/0308569 A1* | 10/2018 | Luellen ................ G16H 20/10 |
| 2019/0253258 A1 | 8/2019 | Thekadath et al. |
| 2020/0160960 A1 | 5/2020 | Truscott et al. |

\* cited by examiner

IDENTIFICATION AND VERIFICATION OF MEDICATION

CROSS-REFERENCE TO RELATED APPLICATIONS

This application is a continuation-in-part of U.S. patent application Ser. No. 16/718,519, filed on Dec. 18, 2019, and titled "IDENTIFICATION AND VERIFICATION OF MEDICATION," which is a divisional application of U.S. patent application Ser. No. 16/276,059, filed on Feb. 14, 2019, and titled "IDENTIFICATION AND VERIFICATION OF MEDICATION," which claims priority to U.S. Provisional Patent Application No. 62/769,132, filed on Nov. 19, 2018, and titled "IDENTIFICATION AND VERIFICATION OF MEDICATION." This Patent Application also claims priority to U.S. Provisional Patent Application No. 63/092,735, filed on Oct. 16, 2020, and titled "SYSTEM FOR IDENTIFICATION AND VERIFICATION OF MEDICATION." The disclosures of these prior Applications are considered part of and are incorporated by reference into this Patent Application.

BACKGROUND

A common form of medication includes pills, capsules, tablets, and/or the like. The medication may be contained in a container. In some cases, a pharmacist, a medication filling device, and/or a pharmacist aided by a medication filling device, and/or the like may fill the container with the medication according to a prescription. Subsequently, the medication may be administered to a person for whom the prescription was written (e.g., by the person, a caregiver, a parent, a medical practitioner, and/or the like).

SUMMARY

In some implementations, a method includes receiving, by a device, prescription information associated with a medication in a container; causing, by the device, a camera device to capture first image data associated with the medication while the medication is in the container and the container is positioned on a receptacle; causing, by the device, an adjusting device to reposition the container on the receptacle; causing, by the device, the camera device to capture second image data associated with the medication while the medication is in the container; processing, by the device and via a neural network, the first image data and the second image data to identify the medication based on depictions of individual units of the medication included in the first image data and the second image data; verifying, by the device, the medication based on the prescription information and an identifier of the medication provided by the neural network; and performing, by the device, an action associated with indicating that the medication is verified according to the prescription information.

In some implementations, a device includes one or more memories and one or more processors, communicatively coupled to the one or more memories, configured to receive prescription information associated with a medication in a container, wherein the container is positioned on a receptacle of the device; obtain a plurality of images of the medication by iteratively: adjusting, via an adjusting device, the container on the receptacle to attempt to reposition individual units of the medication within container, and capturing, via a camera device, image data associated with the medication while the medication is in the container; process, via a neural network, the plurality of images to identify the medication based on one or more depictions of a unit of the individual units; verify the medication based on the prescription information and an identifier of the medication on the unit; and perform an action associated with indicating that the medication is verified according to the prescription information.

In some implementations, a medication analysis system comprises a receptacle that is configured to support a container on a receptacle window; a camera device positioned beneath the receptacle window and configured to have the receptacle window within a field of view of the camera device; an adjusting device configured to move the receptacle to adjust a position of a medication in the container; and a control device configured to identify medication in the container by causing the adjusting device to reposition the container on the receptacle, causing the camera device to capture image data associated with the medication; and processing, via a neural network, the image data to identify the medication; and perform an action associated with identifying the medication.

DETAILED DESCRIPTION

Figure 1:
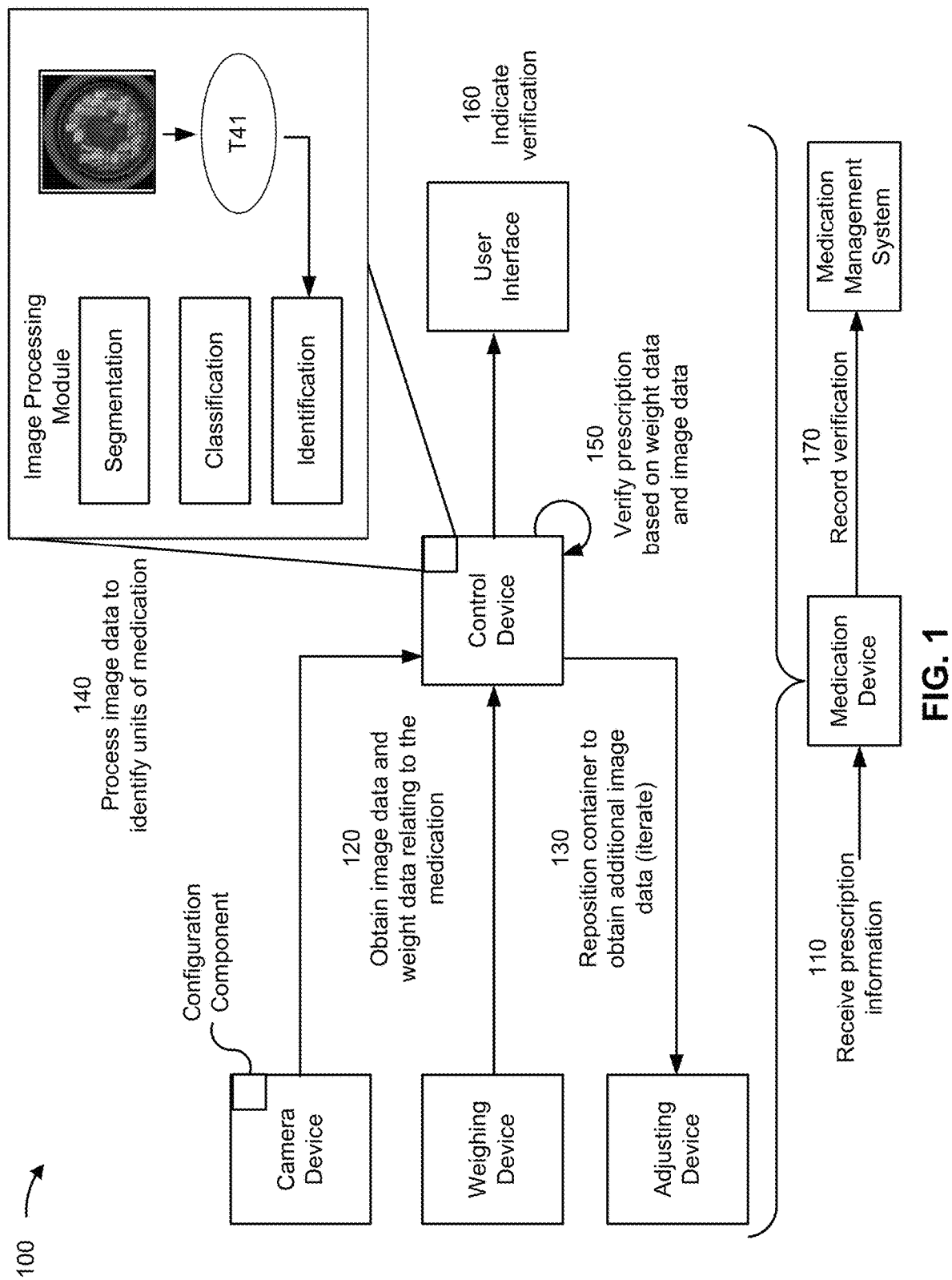
FIG. 1 is a diagram of an example implementation described herein.

The following detailed description of example implementations refers to the accompanying drawings. The same reference numbers in different drawings may identify the same or similar elements.

In some instances, a pharmacist, a medication filling device, and/or a pharmacist aided by a medication filling device, and/or the like may fill a container with medication (e.g., pills, capsules, tablets, and/or the like) according to one or more instructions, such as a prescription. In some cases, there is a need to identify and/or verify the medication in the container (e.g., to ensure that the prescription was filled correctly). In some cases, the medication can be removed from the container and a device can analyze the medication (e.g., perform a chemical analysis) to identify and/or verify the medication. In other cases, a different device can analyze the medication while the medication is in the container by illuminating the container with specific types of light to identify and/or verify the medication. However, these devices are sophisticated devices that require complex components to perform complicated operations, such as open a container, create chemical reactions, produce and focus specific types of light, detect characteristics of the medication, and/or the like. Additionally, the devices require extensive on-board processing resources to identify and/or verify the medication. Moreover, these devices are limited to only analyzing the medication, not the container and/or components of the container, such as a seal of the container.

Some implementations described herein relate to a medication management system for identifying and verifying medication. For example, the medication management system may receive prescription information associated with a medication in a container. The medication management system may cause a camera device to capture first image data associated with the medication while the medication is in the container and the container is positioned on a receptacle.

The medication management system may cause an adjusting device to reposition the container on the receptacle. For example, the adjusting device may jostle, shake, and/or vibrate the container to reposition the medication within the container. By repositioning the medication within the container, the medication management system increases a quantity of unique images captured for an individual unit (e.g., tablet, pill, capsule, vial, and/or the like) of the medication thereby reducing the likelihood of medication stacking (e.g., the positioning of individual units of the medication to cause multiple units of medication to appear, in a captured image, as a single unit of medication).

The medication management system may cause the camera device to capture second image data associated with the medication while the medication is in the container. The medication management system may process, via a neural network, the first image data and the second image data to identify the medication based on depictions of individual units of the medication included in the first image data and the second image data. The medication management system may verify the medication based on the prescription information and an identifier of the medication provided by the neural network.

In this way, the medication management system provides a simple device (e.g., that utilizes uncomplicated components, such as a camera device) for identifying and/or verifying medication. Moreover, the medication management system provides similar accuracy for identifying and/or verifying medication as the complex devices discussed above. This reduces a need for elaborate components to be used to facilitate identifying and/or verifying medication.

Further, the medication management system may obtain weight data associated with the medication and may utilize the weight data to determine an amount of medication in the container. The medication management system may provide information identifying the amount of medication in the container to the pharmacist (e.g., to verify an amount of medication in the container, to cause the pharmacist to refill the prescription, and/or the like), to the individual to whom the medication is administered, to a primary caregiver (e.g., to a family member), to medical personnel, and/or the like. In this way, the medication management system enables bedside tracking capability for use inside medical facilities (e.g., a medical facility that allows a patient to self-administer medication), for use by caregivers (e.g., family members) to track consumption of the medication, and/or the like.

FIG. 1 is a diagram of an example implementation 100 associated with identifying and verifying medication. As shown in FIG. 1, example implementation 100 includes a medication device and a medication management system. The medication device may be a communication and/or computing device and may include one or more receptacles (e.g., for holding a container), one or more camera devices (e.g., to obtain image data concerning medication in the container), one or more receptacle windows (e.g., to allow the one or more camera devices to view the medication in the container and obtain the image data), one or more weighing devices (e.g., to obtain weight data concerning medication in the container), one or more adjustment devices (e.g., to reposition the medication within the container), and/or the like.

The medication management system may be a computing device, a server, a cloud computing device, and/or the like. In some implementations, the medication device and the medication management system may be connected via a network, such as a wired network (e.g., the Internet or another data network), a wireless network (e.g., a wireless local area network, a wireless wide area network, a cellular network, etc.), and/or the like.

Some example implementations described herein concern a single medication device communicating with a single medication management system. In some implementations, a plurality of medication devices may communicate with one or more medication management systems. In some implementations, one or more functions of medication management system may be performed by a medication device instead of, or in addition to, being performed by the medication management system. In some implementations, one or more functions of the medication device may be performed by the medication management system instead of, or in addition to, being performed by the medication device.

In some implementations, a pharmacist, a medication filling device, a pharmacist aided by a medication filling device, and/or the like may fill a container with a medication according to a prescription. The container may be a pill container, a capsule container, a tablet container, a vial, a bottle, and/or the like. The container may be transparent or semi-transparent (e.g. to allow the medication to be seen from outside the container). The container may be filled with the medication and/or additional material, such as padding (e.g., cotton), desiccant, and/or the like. The prescription may be a written direction for the preparation and administration of the medication by a medical practitioner. The prescription may include information that identifies the medication to be filled in the container, a dose of the medication, an amount of the medication to be filled in the container, at least one medication usage instruction, and/or the like.

In some implementations, after filling the container with the prescription, the pharmacist, the medication filling device, and/or the like may apply a closure (e.g., a lid, a cap, a cork, and/or the like), a seal (e.g., a tamper-resistant seal, a hermetic seal, a sanitary seal, a safety seal, and/or the like), and/or the like to the container. Further, the pharmacist, the medication filling device, and/or the like may apply a label to the container that includes information, such as the information included in the prescription, information concerning a pharmacy responsible for filling the prescription (e.g., a name, address, telephone number, email address, and/or the like of the pharmacy), information concerning a manufacturer of the medication (e.g., a name, address, telephone number, email address, and/or the like of the manufacture), information concerning a patient for whom the medication is prescribed (e.g., a name, address, telephone number, email address, and/or the like of the patient), an identifier (e.g., an identification string, a bar code, a quick response (QR) code, and/or the like) associated with the prescription, information concerning the medication (e.g., a description of one or more characteristics of the medication), and/or the like.

In some implementations, a user of the medication device, such as the pharmacist, the patient, and/or the like may want to identify and/or verify the medication in the container and/or verify the integrity of the seal of the container. In some implementations, the user may place the container in a receptacle of the medication device to have the medication device facilitate identifying and/or verifying the medication in the container and/or verifying the integrity of the seal of the container.

As shown by reference number 110, the medication device receives prescription information relating to the medication in the container. The prescription information may include the information included on the label of the container and/or the information included in the prescription. For example, the prescription information may include an identifier of the medication, information identifying a dose of the medication, information identifying an amount of the medication, and/or the like. The information identifying the amount of the medication may include information identifying a quantity of the medication in the container, a weight of a unit (e.g., a pill, a capsule, a tablet, and/or the like) of the medication, a total weight of the medication not including a weight of the container, a total weight of the medication including the weight of the container, and/or the like.

In some implementations, the user of the medication device may cause the medication device to obtain the prescription information by interacting with the medication device. For example, the user may enter, via a user interface of the medication device, information, such as the identification string associated with the prescription, into the medication device. The medication device may perform a lookup in a data structure based on the identification string to obtain the prescription information.

As another example, the user may present the label of the container to the medication device, such as position the label in a field of view of a camera device of the one or more camera devices, and the medication device may cause the camera device to obtain image data of the label. The medication device may include one or more components to facilitate positioning the label in the field of view of the camera device (e.g., an arm to rotate the container so that the label is pointed toward the camera device, a guide to position the container in front of the camera device, and/or the like). The medication device may use an image processing technique to process the image data to determine the bar code and/or the QR code of the label. The medication device may perform a lookup in a data structure based on the bar code and/or the QR code to obtain the prescription information.

As shown by reference number 120, the medication management system obtains image data and weight data relating to the medication. The medication device may obtain image data relating to the medication while the medication is in the container. The image data may include image data concerning a size, a shape, a color, a pattern, a shading, a texture, a labeling, a luminance, and/or the like of at least one individual unit of the medication. In some implementations, the medication device causes at least one camera device, of the one or more camera devices, to obtain the image data. For example, the medication device may determine that the container has been placed in a receptacle of the one or more receptacles (e.g., based on receiving weight data from a weighing device of the one or more weighing devices, as described in greater detail below). The medication device may cause the at least one camera device to obtain the image data based on determining that the container has been placed in the receptacle.

The at least one camera device may obtain the image data via at least one receptacle window of the one or more receptacle windows (e.g., at least one receptacle window associated with the receptacle). The at least one receptacle window may be configured to support the container while the at least one camera device obtains the image data. The at least one receptacle window may allow the at least one camera device to point at a bottom of the container, at least one side of the container, a top of the container, and/or the like to obtain the image data. For example, the at least one camera device may be positioned under the receptacle window, and the receptacle window may be within a field of view of the at least one camera device. As another example, when causing the at least one camera device to obtain the image data, the medication device may cause the at least one camera device to determine when the container is in a field of view of the at least one camera device (e.g., the camera device may use object recognition software to recognize the container as the at least one camera device captures preview image data) and to focus on the medication in the container (e.g., adjust a focal length of the at least one camera device to focus on the medication).

In some implementations, the medication device causes light to illuminate the container. For example, the medication device may be designed to allow ambient light to illuminate the container (e.g. via the one or more receptacle windows). As another example, the medication device may include one or more light sources (e.g., one or more light emitting diodes, one or more incandescent bulbs, one or more fluorescent lights, and/or the like) that produce the light. The light may be associated with one or more colors (e.g., "white" light, "red" light, "blue" light, "yellow" light, and/or the like). The medication device may cause the at least one camera device to obtain the image data while the container is illuminated with the light.

In some implementations, the camera device includes a configuration component. The configuration component may be configured to control the amount of light illuminating the container, a color of the light illuminating the container, a filter setting of the camera device, a capture setting of the camera device, a zoom setting of the camera device, and/or the like. The medication device may cause the light to illuminate the container based on sending a message to the configuration component. The message may include information identifying an amount of light to be emitted by the one or more light sources, a color or wavelength of the light, a filter setting, a capture setting, a zoom setting, and/or the like. The configuration component may cause the one or more light sources to emit light to illuminate the container and/or may cause the camera device to obtain the image data based on the information included in the message.

In some implementations, the medication device obtains a respective image for each of a plurality of containers placed in a plurality of container receptacles of the medication device. In some implementations, the medication device includes a plurality of camera devices. Each camera device, of the plurality of camera devices, may be associated with a respective container receptacle of the plurality of container receptacles. The medication device may cause each camera device to capture an image of the respective container placed in the respective container receptacle associated with each camera device in a manner similar to that described above. Alternatively, and/or additionally, the medication device may cause a single camera device to capture a respective image of each container of the plurality of containers.

The medication device may obtain weight data relating to the medication while the medication is in the container. The weight data may include weight data concerning the container, the medication, the label of container, the closure, the seal, and/or the like. In some implementations, the medication device causes at least one weighing device, of the one or more weighing devices, to obtain the weight data. In some implementations, the at least one weighing device obtains weight information concerning a combined weight of the medication, the container, the label of container, the closure, the seal, and/or the like. The medication device may process the weight information (e.g., process the weight information using a tare functionality) to determine the weight data (e.g., determine a weight of just the medication).

In some implementations, the medication device obtains respective weight data for a plurality of containers of medication. In some implementations, the medication device utilizes a plurality of weighing devices to obtain the respective weight data for the plurality of containers of medication. Alternatively, and/or additionally, the medication device obtains a combined weight data for the plurality of containers of medication. For example, the medication device may utilize a single weighing device to obtain a combined weight data associated with one or more containers, the medication contents, and optionally the label of container, the closure, the seal, and/or the like of each of the plurality of containers of medication.

In some implementations, the medication device verifies a fill weight of the medication. The fill weight may correspond to the combined weight of the medication, the container, the label of the container, the closure, the seal, and/or the like. The medication device may verify the fill weight based on a comparison between a fill weight determined based on the weight data and a calculated fill weight. The medication device may determine the calculated fill weight based on a weight of an empty container and a weight of an individual unit of the medication.

The medication device may determine a weight of the empty container. For example, the medication device may determine the weight of the empty container based on information input by a user via a user interface associated with the medication device, based on accessing a data structure (e.g., a database, a table, a list, and/or the like) storing weight information for different types and/or sizes of containers, based on a user putting an empty container in the container receptacle and obtaining weight data from the one or more weighing devices, and/or the like. The medication device may determine a weight of an individual unit of the medication based on the prescription information and/or based on accessing a data structure storing weight data for individual units of medication. The medication device may determine a quantity of units of the medication included in the container based on the prescription information. The medication device may calculate a total weight of the medication based on the quantity of units and the weight of an individual unit of the medication (e.g., multiple the weight of an individual unit by the quantity of units). The medication device may determine the calculated fill weight based on the weight of the empty container and the total weight of the medication (e.g., add the weight of the empty container to the total weight of the medication). The medication device may compare the calculated fill weight and the actual fill weight.

The medication device may verify the fill weight of the medication based on comparing the calculated fill weight and the actual fill weight. For example, the medication device may verify the fill weight based on the calculated fill weight being the same as the actual fill weight, based on a difference between the calculated fill weight and the actual fill weight satisfying a threshold amount, and/or the like. In some implementations, the medication device provides a notification associated with verifying the fill weight of the medication. For example, the medication device may cause information indicating that the fill weight of the medication is verified to be displayed via a user interface associated with the medication device. As shown by reference number 130, the medication device repositions the container to obtain additional image data relating to the medication. The medication device may include an adjusting device that repositions the container on the container receptacle. For example, the adjusting device may vibrate, shake, and/or jostle the container to cause the medication to be rearranged and/or repositioned within the container. In some implementations, the adjusting device comprises a vibration mechanism that is configured to move the container on the container receptacle. For example, the adjusting device may include one or more load cells that are positioned around a perimeter of the receptacle window and configured to vibrate the container on the container receptacle. In some implementations, the one or more load cells are coupled to the medication device via respective load cell mounts that provide a cantilever action.

The medication device may cause the adjusting device to reposition the container to cause the medication to be rearranged and/or repositioned within the container based on obtaining the initial image data and/or the weight data relating to the medication. The medication device may cause the camera device to obtain the additional image data based on the adjusting device repositioning the container.

In some implementations, prior to causing the at least one camera device to capture the additional image data, the medication device modifies a configuration setting of the at least one camera device. For example, the medication device may adjust a polarization of a lens of the at least one camera device, a light filter of a lens of the at least one camera device, a zoom setting of the at least one camera device, a wavelength of a light emitter associated with the at least one camera device, and/or the like. The medication device may adjust the polarization of the lens to reduce reflected light depicted in images associated with the image data. The medication device may adjust the light filter of the lens to filter a particular wavelength of light from images associated with the image data. The medication device may adjust the zoom setting to adjust dimensions of the field of view of the at least one camera device. The medication device may adjust the wavelength of the light emitter to adjust a characteristic (e.g., a color) of light in images associated with the image data.

Alternatively, and/or additionally, the receptacle window may include one or more adjustable filters. Prior to causing the at least one camera device to capture the additional image data, the medication device may adjust the polarized lens, the light filter, the lens, the light emitter, and/or the one or more adjustable filters.

In some implementations, the medication device causes the at least one camera device to capture a plurality of additional image data corresponding to a plurality of images of the medication while the medication is in the container. The medication device may iteratively process images, of the plurality of images, after corresponding additional image data is captured by the at least one camera device. The images may be obtained until the medication is identified in an image of the plurality of images and/or until a predetermined quantity of images are obtained. The predetermined quantity may be associated with a configuration of a neural network used to process the image data, as described in greater detail below.

In some implementations, the medication device determines information concerning the medication based on the image data and/or the weight data. For example, the medication device may process the image data and/or weight data to identify the medication, a dose of the medication, an amount of the medication in the container, and/or the like.

As shown by reference number 140, the medication device may process the image data to identify units of the medication. In some implementations, the medication device utilizes a machine learning model to process the image data (e.g., the image data and the additional image data) to identify the units of the medication. For example, the medication device may process, via a neural network of a machine learning model, the image data and the additional image data to identify the medication based on depictions of individual units of the medication included in the image data and the additional image data. The neural network may comprise a convolutional neural network that is configured to segment the image data and the additional image data into the depictions of the individual units, determine classification scores of the depictions that are associated with identifying the medication based on corresponding ones of the individual units, and identify the medication based on the classification scores.

In some implementations, the machine learning model includes an object detection model. The object detection model may process the image data and the additional image data to determine a plurality of bounding boxes corresponding to locations of the individual units within images included in the image data and/or the additional image data. The medication device may segment the images to generate the depictions of the individual units based on the plurality of bounding boxes. The machine learning model may process one or more of the depictions of the individual units to determine the classification scores. For example, the medication device may select one or more of the depictions of the individual units based on one or more characteristics (e.g., a size of the individual unit within an image, an amount of the individual unit visible within the image, a position of the individual unit within the image, and/or the like) associated with the depictions of the individual units. The medication device may process the selected depictions of the individual units to determine classification scores associated with the selected depictions. The classification scores may indicate a likelihood that the individual units correspond to an individual unit of a particular type of medication. The medication device may identify the medication as the particular type of medication based on the classification scores. For example, the medication device may identify the medication as the particular type of medication based on the classification score satisfying a classification score threshold.

Alternatively, and/or additionally, the medication management system may process the image data to identify units of the medication. For example, the medication management system may utilize a machine learning model to process the image data to identify units of the medication in a manner similar to that described above. In some implementations, the medication device and/or the medication management system may process the image data to identify the units of the medication for each of a plurality of containers of medication in a manner similar to that described above.

In some implementations, the medication device generates and/or trains the machine learning model. For example, the medication device may obtain historical information concerning medication, historical image data, and/or historical weight data (hereinafter collectively referred to as the "historical information") to generate and/or train the machine learning model. In some implementations, the medication device may process the historical information to train the machine learning model to identify a medication, a dose of medication, and an amount of medication, and/or the like, based on image data and weight data and/or to determine an identification confidence level, in a manner similar to that described below with respect to FIG. 3. An identification confidence level may indicate a predicted level of accuracy concerning identification of a medication, a dose of medication, an amount of medication, and/or the like. For example, a low identification confidence level may indicate a low predicted level of accuracy (e.g., less than a particular percentage accuracy), a high identification confidence level may indicate a high predicted level of accuracy (e.g., greater than or equal to the particular percentage accuracy), and/or the like.

In some implementations, a different device (e.g., the medication management system, a server device, and/or the like) generates and/or trains the machine learning model. The medication device may obtain the machine learning model from the different device. For example, the different device may send (e.g., on a scheduled basis, on an on-demand basis, on a triggered basis, and/or the like) the machine learning model to the medication device.

As shown by reference number 150, the medication device verifies the prescription based on the weight data and the image data. In some implementations, the medication device verifies the medication based on the prescription information and the information concerning the medication. For example, the medication device may determine that the medication has been verified if an identification of the medication, the dose, the amount of the medication, and/or the like included in the information concerning the medication corresponds (e.g., matches, matches within a threshold, and/or the like) to the prescription information. Moreover, the medication device may confirm the verification of the medicine if the identification confidence level satisfies a threshold (e.g., is equal to or greater than the threshold). Additionally, or alternatively, the medication device may determine that the medication has not been verified if the identification of the medication, the dose, the amount of the medication, and/or the like included in the information concerning the medication does not correspond (e.g., does not match, does not match within a threshold, and/or the like) to the prescription information. Moreover, the medication device may determine that the medication has not been verified if the identification confidence level does not satisfy a threshold (e.g., is less than the threshold).

As another example, the medication device may verify the medication by: determining that an identifier of the medication included in the prescription information matches an identifier of the medication included in the information concerning the medication, determining that a dose of the medication identified in the prescription information matches a dose of the medication identified in the information concerning the medication, and/or determining that an amount of the medication identified in the prescription information corresponds, within a threshold, to an amount of the medication identified in the information concerning the medication.

In some implementations, the medication device may include a determination of whether the medication has been verified to the information concerning the medication. In some implementations, the medication device, after determining whether the medication has been verified, may cause the machine learning model to be updated. For example, the medication device may cause the machine learning model to be updated (e.g., cause the machine learning model to be retrained) based on the image data, the weight data, the prescription information, the information concerning the medication, and/or the like.

In some implementations, the medication device verifies the integrity of a seal of the container based on the medication being verified. For example, the medication device may obtain additional image data relating to the seal of the container. In some implementations, the medication device may cause the at least one camera device to obtain the additional image data in a similar manner as described above in relation to the medication device obtaining the image data. For example, the medication device may determine that the container has been placed in the receptacle and may cause the at least one camera device to obtain the additional image data. In some implementations, the user may place the container upside-down in the receptacle to allow a particular camera device, of the one or more camera devices, to obtain the additional image data (e.g., to allow the particular camera device, which may point upwards through a receptacle window that is at the bottom of the receptacle, to point at the seal of the container when the container is placed upside-down). In some implementations, the medication device may include one or more components to facilitate positioning the seal in the field of view of the particular camera device (e.g., an arm to rotate the container so that the seal is pointed toward the camera device, a guide to position the seal in front of the camera device, and/or the like).

The medication device may determine information concerning the seal to verify the integrity of the seal. The medication device may determine the information concerning the seal based on the additional image data. For example, the medication device may process the additional image data to determine the information concerning the seal, which may include information concerning the integrity of the seal (e.g., whether the seal is intact, has one or more tears, has one or more holes, shows signs of seal tampering, shows signs of seal failure, and/or the like).

In some implementations, the medication device may determine the information concerning the seal using a second machine learning model. In some implementations, the medication device receives, generates, and/or trains the second machine learning model in a similar manner as described above and/or in a manner similar to that described below with respect to FIG. 3. In some implementations, the medication device processes the additional image data to determine integrity issues concerning seals and/or to determine an integrity confidence level. An integrity confidence level may indicate a predicted level of accuracy concerning a determination of an integrity issue. For example, a low integrity confidence level may indicate a low predicted level of accuracy (e.g., less than a particular percentage accuracy), a high integrity confidence level may indicate a high predicted level of accuracy (e.g., greater than or equal to the particular percentage accuracy), and/or the like.

The medication device may use the second machine learning model to determine, based on the additional image data, whether the seal has an integrity issue. In some implementations, the medication device, after determining whether the seal has an integrity issue, may cause the second machine learning model to be updated. For example, the medication device may cause the second machine learning model to be updated (e.g., cause the second machine learning model to be retrained) based on the additional image data, the information concerning the seal, and/or the like.

As shown by reference number 160, the medication device indicates whether the medication and/or the seal has been verified. The medication device may generate a message concerning the medication and the seal. In some implementations, the medication device generates the message based on the information concerning the medication and the information concerning the seal. The message may include information, such as information indicating whether the medication has been verified, whether the integrity of the seal has been verified, and/or the like. Alternatively, and/or additionally, the message may include one or more instructions, such as instructions associated with how much of the medication a user of the medication device is to take, instructions associated with notifying a manufacture of the medication about possible tampering of the medication and/or seal, and/or the like. In some implementations, the message includes one or more warnings, such as warnings that the medication may be counterfeit, warnings that the integrity of the seal has been compromised, and/or the like; and/or the like.

The medication device may cause a presentation of the message (e.g., cause a display to present the message, cause a speaker to present the message, and/or the like). The medication device may cause the presentation of the message via a display of the medication device, a speaker of the medication device, and/or the like. For example, the medication device may generate, based on the message, voice data using a text-to-speech technique and cause the speaker of the medication device to emit the voice data.

In some implementations, the medication device causes a different device to present the message (e.g., cause a display of the different device to present the message, cause a speaker of the different device to present the message, and/or the like). For example, the medication device may determine, based on the prescription information, an identifier (e.g., a telephone number, an internet protocol (IP) address, and/or the like) of the different device (e.g., a user device of the patient, a client device of the pharmacy and/or manufacture, and/or the like). The medication device may send the message, based on the identifier of the different device, to the different device. The different device, based on receiving the message, may display the message on the display of the different device and/or emit the message via the speaker of the different device.

In some implementations, a user may use the medication device to facilitate the user removing a proper dosage amount of the medication from the container. For example, a user of the medication device may remove an amount of medication from the container after viewing and/or hearing the presentation of the message and place the container in a receptacle of the medication device for the medication device to verify that the amount of medication is correct.

Accordingly, the medication device may obtain further image data relating to the medication. For example, the medication device may cause the at least one camera device to obtain the further image data in a similar manner as described above in relation to the medication device obtaining the image data and the additional image data.

The medication device may obtain further weight data relating to the medication. In some implementations, the medication device causes the at least one weighing device to obtain the further weight data in a similar manner as described above in relation to the medication device obtaining the weight data. For example, the medication device may cause the at least one weighing device to obtain the further weight data after the user places the container in the receptacle of the medication device.

The medication device may determine the amount of medication removed from the container. In some implementations, the medication device processes the further image data and the further weight data to determine additional information concerning the medication, in a similar manner as described above, to facilitate determining the amount of medication removed from the container. For example, the medication device may process the further image data and the further weight data using the machine learning model to identify the medication (e.g., verify that the same medication is being analyzed) and a new amount of the medication. The medication identification and verification platform may compare the new amount of the medication and the amount of the medication (e.g., an original amount of the medication before the user removed medication from the container) included in the information concerning the medication to determine the amount of medication removed from the container. The medication device may include information identifying the amount of medication removed from the container, information identifying the new amount of the medication, information identifying the amount of the medication, and/or the like in additional information concerning the medication.

The medication device may generate an additional message concerning the medication based on the additional information concerning the medication. The additional message may include information, such as information on whether the amount of medication removed from the container is correct, information on how much medication is left in the container, and/or the like.

The medication device may cause a presentation of the additional message (e.g., cause a display to present the additional message, cause a speaker to present the additional message, and/or the like). In some implementations, the medication device causes the medication device and/or a different device to present the additional message in a similar manner as described above.

In some implementations, a user may use the medication device to facilitate the user removing a proper dosage amount of medication from a plurality of containers. The user may place the plurality of containers in a respective container receptacle, of a plurality of container receptacles of the medication device. The medication device may verify that the user is removing a proper dosage amount of medication from each container, of the plurality of containers, in a manner similar to that described above.

In some implementations, the medication device is utilized to monitor consumption of the medication. For example, the medication device may be located in a person's home and/or in a medical facility (e.g., a medical facility and/or another type of facility that allows a patient to self-administer a medication) and the medication device may monitor the consumption of the medication to track consumption of the medication, to determine when to refill a prescription for the medication, to automatically refill the prescription, and/or the like.

In some implementations, the medication device monitors consumption of the medication based on determining a quantity of units of the medication included in the container. In some implementations, the medication device may utilize the calculated fill weight to determine the quantity of units of the medication included in the container. For example, the medication device may determine the quantity of units of the medication included in the container by dividing the calculated fill weight by the weight of an individual unit of the medication.

In some implementations, the medication device periodically monitors consumption of the medication to determine whether a person is taking and/or being administered the medication in accordance with the prescription. For example, the medication device may determine a frequency (e.g., hourly, every four hours, daily, twice a day, and/or the like) at which a quantity of the medication is to be taken and/or administered to a person for whom the prescription was written based on the prescription information. The medication device may periodically determine the quantity of units in the container based on the frequency at which the quantity of the medication is to be taken and/or administered to the person. The medication device may compare the quantity of units and a previously determined quantity of units to determine whether the medication was taken by and/or administered to the person. The medication device may provide information indicating whether the medication was taken by and/or administered to the person to a client device (e.g., a client device associated with the person, a caregiver, medical personnel, a family member, and/or the like). In this way, the medication device may enable medical personnel, family members, caregivers, and/or the like to track a person's consumption of a medication.

In some implementations, the medication device determines that the medication is to be refilled based on the quantity of units in the container. For example, the medication device may determine that the quantity of units in the container satisfies a threshold quantity (e.g., a threshold quantity set by the pharmacist, a doctor, the person, and/or the like). The medication device may determine that the medication is to be refilled based on the quantity of units satisfying the threshold quantity.

In some implementations, the medication device may determine whether there are any refills remaining based on the prescription information. The medication device may provide information indicating that the medication is to be refilled to a client device (e.g., a client device associated with the person, a client device associated with the pharmacist, and/or the like) when there are refills remaining.

In some implementations, the medication device automatically requests that the prescription be refilled when there are no refills remaining. For example, the medication device may provide information requesting the prescription to be refilled, information identifying a quantity of units of the medication remaining, information identifying the person for which the prescription was written, information identifying a pharmacy to be used to refill the prescription, and/or the like to client device associated with a medical professional identified in the prescription information.

As shown by reference number 170, the medication management system records verification of the medication and/or the seal. For example, the medication device may provide the information described herein to the medication management system. The medication management system may store the information in a memory associated with the medication management system based on receiving the information from the medication device.

In some implementations, information described herein may be obtained from and/or stored in a blockchain. A blockchain is a distributed database that maintains a continuously-growing list of records, called blocks, that may be linked together to form a chain. Each block in the blockchain may contain information (e.g., a timestamp, a link, etc.) relating it to a previous block and/or transaction in the blockchain. The blocks may be secured from tampering and revision. In addition, a blockchain may include a secure transaction ledger database shared by parties participating in an established, distributed network of computers. A blockchain may record a transaction (e.g., an exchange or transfer of information) that occurs in the network, thereby reducing or eliminating the need for trusted/centralized third parties. Exemplary embodiments can employ private (e.g., closed) or public (e.g., open) blockchain environments. In some cases, the parties participating in a transaction may not know the identities of any other parties participating in the transaction but may securely exchange information. Further, the distributed ledger may correspond to a record of consensus with a cryptographic audit trail that is maintained and validated by a set of independent computers.

For example, the prescription information may be stored in a blockchain and the medication device and/or the medication management system may obtain the prescription information from the blockchain. As another example, the medication device and/or the medication management system may store the prescription information, the information concerning the medication, the information concerning the seal, the additional information concerning the medication, and/or the like in the blockchain. The blockchain may be accessible by one or more devices associated with manufacturing, filling, or distributing the medication. In this way, a record regarding the integrity of the medication, the seal, the container, and/or the like may be updated by every entity that handles the medication, the seal, the container, and/or the like.

Some example implementations described herein concern the medication device performing one or more functions (e.g., identifying and verifying the medication, verifying the integrity of the seal, determining the amount of medication removed from the container, and/or the like), but some implementations include the medication management system performing the one or more functions. For example, in some implementations, the medication device provides the image data and the additional image data to the medication management system and the medication management system performs all of the one or more functions. Additionally, or alternatively, some example implementations described herein concern the medication device generating and/or causing presentation of messages, but some implementations include the medication management system generating and/or causing the messages.

In this way, the medication device provides a simple device (e.g., that utilizes uncomplicated components, such as a camera device and a weighing device) for identifying and/or verifying medication. Moreover, the medication device provides similar accuracy for identifying and/or verifying medication as the complex devices discussed above. This reduces a need for elaborate components to be used to facilitate identifying and/or verifying medication. Moreover, the medication device may send data to the medication management system for the medication identification and verification platform to analyze the data, which reduces a need for extensive processing resources to be located where the medication and/or container is being analyzed to facilitate identifying and/or verifying medication. Further, the medication device facilitates determining the integrity of a seal of the container using the same, uncomplicated components that are used to facilitate identifying and/or verifying the medication.

As indicated above, FIG. 1 is provided as an example. Other examples may differ from what is described with regard to FIG. 1. The number and arrangement of devices shown in FIG. 1 are provided as an example. In practice, there may be additional devices, fewer devices, different devices, or differently arranged devices than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) shown in FIG. 1 may perform one or more functions described as being performed by another set of devices shown in FIG. 1.

Figure 2A:
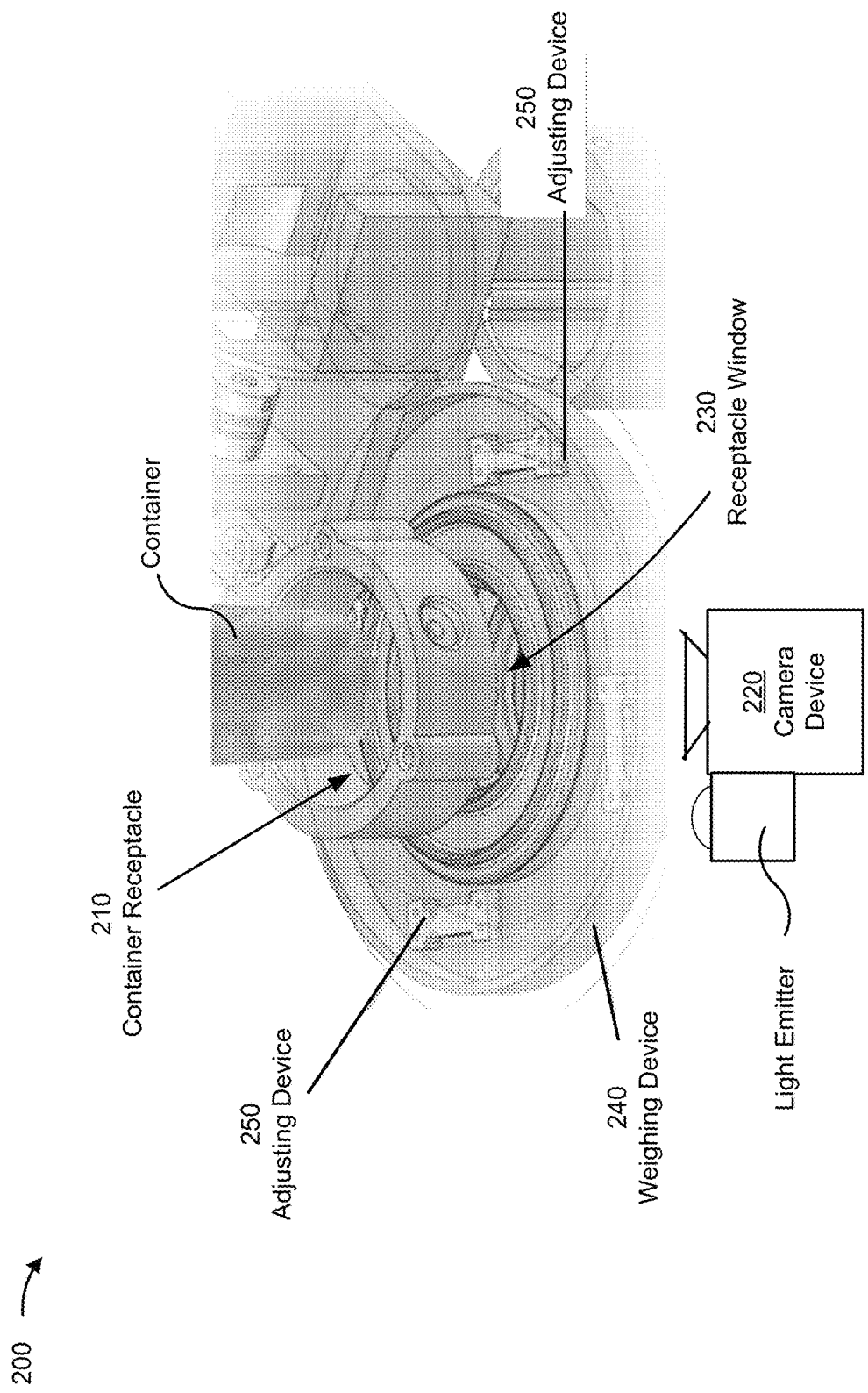
FIGS. 2A-2B are diagrams of an example medication device described herein.
Figure 2B:
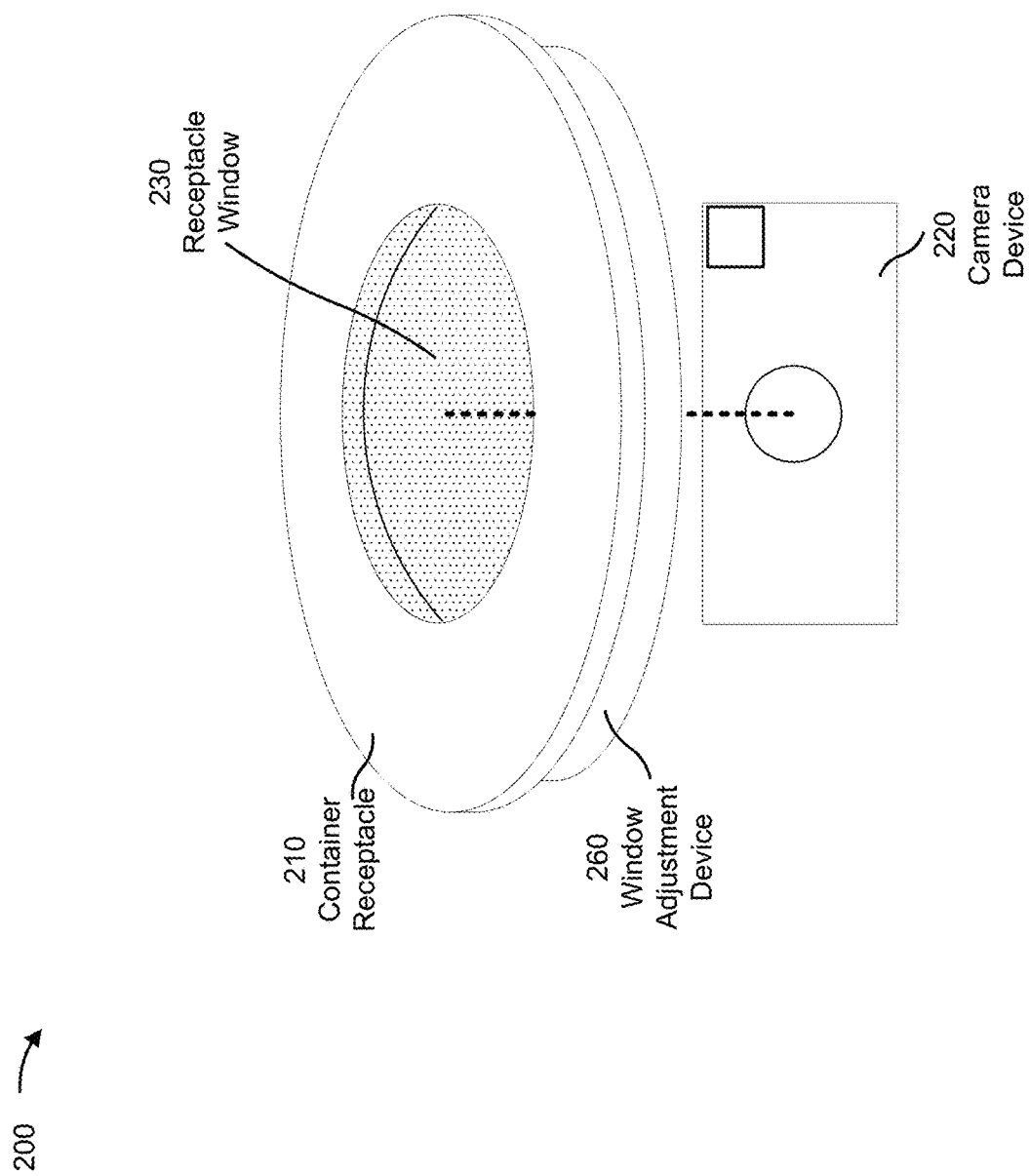

FIGS. 2A-2B are diagrams of an example medication device 200 described herein. As shown in FIG. 2A, medication device 200 may be a communication and/or computing device and may include one or more container receptacles 210 (e.g., to hold one or more containers), one or more camera devices 220 (e.g., to obtain image data concerning medication in the container and/or a seal of the container), one or more receptacle windows 230 (e.g., to facilitate the one or more camera devices 220 obtaining the image data), a weighing device 240, an adjusting device 250, and/or the like that perform functions, such as functions described above in connection with FIG. 1.

As shown in FIG. 2B, a container receptacle 210, of the one or more container receptacles 210, may include a receptacle window 230, of the one or more receptacle windows 230, in and/or on the container receptacle 210. A camera device 220, of the one or more camera devices 220, may be contained within the medication device 200 and point at the receptacle window 230 to obtain image data of medication in a container held in the container receptacle 210. The container receptacle 210 and/or the receptacle window 230 may be attached and/or disposed on a weighing device 240, of one or more weighing devices 240 of medication device 200, that obtains weight data concerning the medication in the container.

As also shown in FIG. 2B, the medication device includes a window adjustment device 260 configured to modify a configuration setting of the at least one camera device 220 and/or a configuration of the receptacle window 230. For example, the window adjustment device 260 may be configured to adjust a polarization of a lens of the at least one camera device 220, a light filter of a lens of the at least one camera device 220, a zoom setting of the at least one camera device 220, a wavelength of a light emitter associated with the at least one camera device 220, and/or the like. Alternatively, and/or additionally, the receptacle window 230 may include one or more adjustable filters and the window adjustment device 260 may be configured to adjust the one or more adjustable filters.

As indicated above, FIGS. 2A-2B are provided as an example. Other examples may differ from what is described with regard to FIGS. 2A-2B. The number and arrangement of devices shown in FIGS. 2A-2B are provided as an example. In practice, there may be additional devices, fewer devices, different devices, or differently arranged devices than those shown in FIGS. 2A-2B. Furthermore, two or more devices shown in FIGS. 2A-2B may be implemented within a single device, or a single device shown in FIGS. 2A-2B may be implemented as multiple, distributed devices. Additionally, or alternatively, a set of devices (e.g., one or more devices) shown in FIGS. 2A-2B may perform one or more functions described as being performed by another set of devices shown in FIGS. 2A-2B.

Figure 3:
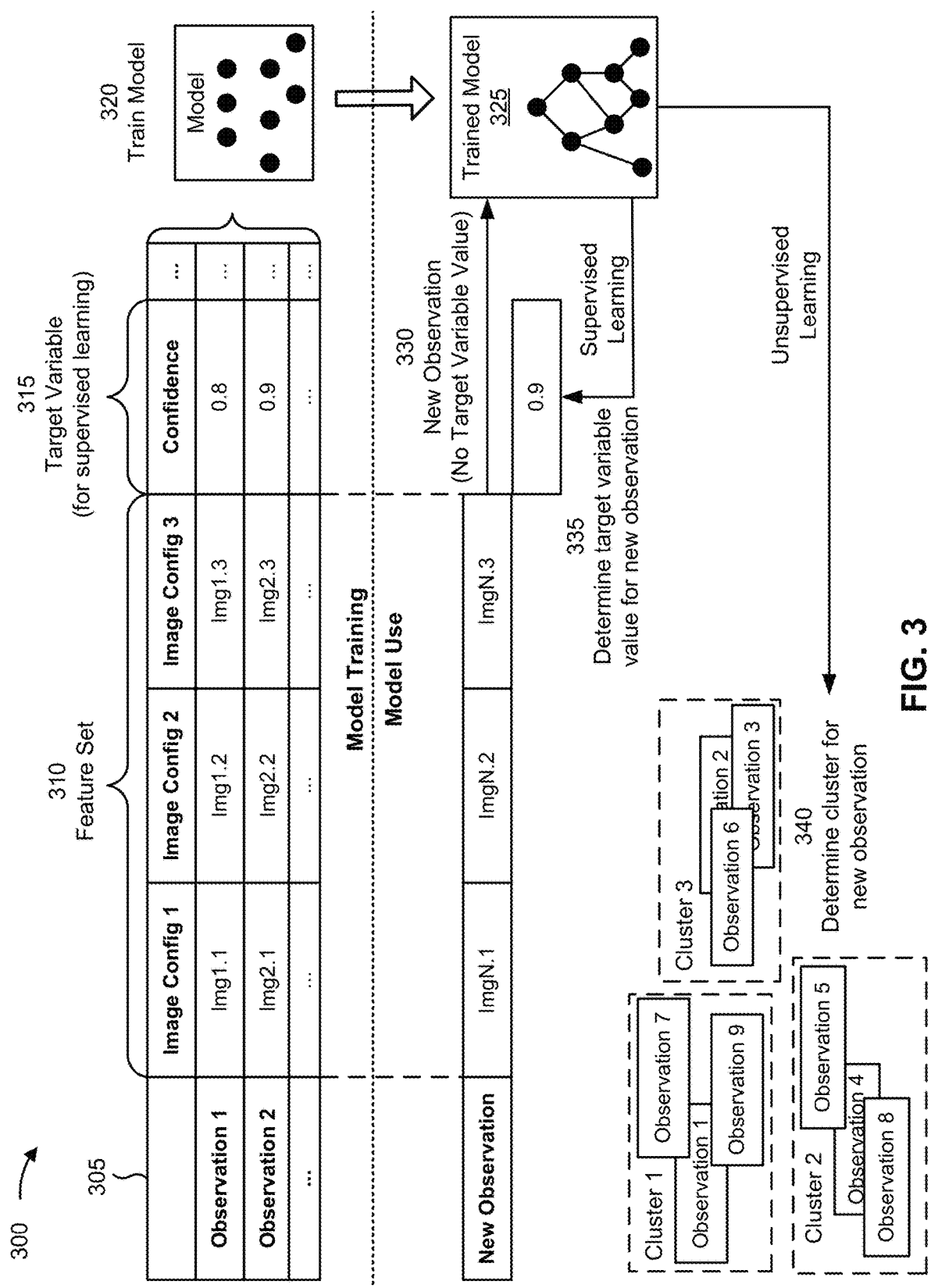
FIG. 3 is a diagram illustrating an example of training and using a machine learning model in connection with identifying and verifying medications.

FIG. 3 is a diagram illustrating an example 300 of training and using a machine learning model in connection with identifying and verifying medications. The machine learning model training and usage described herein may be performed using a machine learning system. The machine learning system may include or may be included in a computing device, a server, a cloud computing environment, or the like, such as the medication management system described in more detail elsewhere herein.

As shown by reference number 305, a machine learning model may be trained using a set of observations. The set of observations may be obtained from training data (e.g., historical data), such as data gathered during one or more processes described herein. In some implementations, the machine learning system may receive the set of observations (e.g., as input) from medication management system, as described elsewhere herein.

As shown by reference number 310, the set of observations includes a feature set. The feature set may include a set of variables, and a variable may be referred to as a feature. A specific observation may include a set of variable values (or feature values) corresponding to the set of variables. In some implementations, the machine learning system may determine variables for a set of observations and/or variable values for a specific observation based on input received from medication management system. For example, the machine learning system may identify a feature set (e.g., one or more features and/or feature values) by extracting the feature set from structured data, by performing natural language processing to extract the feature set from unstructured data, and/or by receiving input from an operator.

As an example, a feature set for a set of observations may include a first feature of a first image configuration (e.g., Image Config 1, as shown in FIG. 3), a second feature of a second image configuration (e.g., Image Config 2, as shown in FIG. 3), a third feature of a third image configuration (e.g., Image Config 3, as shown in FIG. 3), and so on. The different image configurations may be associated with repositioning the container, repositioning the camera device, adjusting an amount of light shining on the container, adjusting a setting (e.g., a filter setting, a focus setting, and/or the like) of the camera device, and/or the like. As shown, for a first observation, the first feature may have a value of a first image configuration identifier (e.g., Img1.1, as shown in FIG. 3), the second feature may have a value of a second image configuration identifier (e.g., Img1.2, as shown in FIG. 3), the third feature may have a value of a third image configuration identifier (e.g., Img1.3, as shown in FIG. 3), and so on. These features and feature values are provided as examples and may differ in other examples.

As shown by reference number 315, the set of observations may be associated with a target variable. The target variable may represent a variable having a numeric value, may represent a variable having a numeric value that falls within a range of values or has some discrete possible values, may represent a variable that is selectable from one of multiple options (e.g., one of multiples classes, classifications, or labels) and/or may represent a variable having a Boolean value. A target variable may be associated with a target variable value, and a target variable value may be specific to an observation. In example 300, the target variable is a confidence score (e.g., Confidence, as shown in FIG. 3) indicating a likelihood of the medication being correctly identified, which has a value of 0.8 (e.g., 80%) for the first observation. Alternatively, and/or additionally, the target variable may be an identification of a medication associated with the observation.

The target variable may represent a value that a machine learning model is being trained to predict, and the feature set may represent the variables that are input to a trained machine learning model to predict a value for the target variable. The set of observations may include target variable values so that the machine learning model can be trained to recognize patterns in the feature set that lead to a target variable value. A machine learning model that is trained to predict a target variable value may be referred to as a supervised learning model.

In some implementations, the machine learning model may be trained on a set of observations that do not include a target variable. This may be referred to as an unsupervised learning model. In this case, the machine learning model may learn patterns from the set of observations without labeling or supervision, and may provide output that indicates such patterns, such as by using clustering and/or association to identify related groups of items within the set of observations.

As shown by reference number 320, the machine learning system may train a machine learning model using the set of observations and using one or more machine learning algorithms, such as a regression algorithm, a decision tree algorithm, a neural network algorithm, a k-nearest neighbor algorithm, a support vector machine algorithm, or the like. After training, the machine learning system may store the machine learning model as a trained machine learning model 325 to be used to analyze new observations.

As shown by reference number 330, the machine learning system may apply the trained machine learning model 325 to a new observation, such as by receiving a new observation and inputting the new observation to the trained machine learning model 325. As shown, the new observation may include a first feature of a first image configuration (e.g., Image Config 1, as shown in FIG. 3), a second feature of a second image configuration (e.g., Image Config 2, as shown in FIG. 3), a third feature of a third image configuration (e.g., Image Config 3, as shown in FIG. 3), and so on, as an example. The machine learning system may apply the trained machine learning model 325 to the new observation to generate an output (e.g., a result). The type of output may depend on the type of machine learning model and/or the type of machine learning task being performed. For example, the output may include a predicted value of a target variable, such as when supervised learning is employed. Additionally, or alternatively, the output may include information that identifies a cluster to which the new observation belongs and/or information that indicates a degree of similarity between the new observation and one or more other observations, such as when unsupervised learning is employed.

As an example, the trained machine learning model 325 may predict a value of 0.9 for the target variable of a confidence score for the new observation, as shown by reference number 335. Based on this prediction, the machine learning system may provide a first recommendation, may provide output for determination of a first recommendation, may perform a first automated action, and/or may cause a first automated action to be performed (e.g., by instructing another device to perform the automated action), among other examples.

In some implementations, the trained machine learning model 325 may classify (e.g., cluster) the new observation in a cluster, as shown by reference number 340. The observations within a cluster may have a threshold degree of similarity. As an example, if the machine learning system classifies the new observation in a first cluster (e.g., a high confidence score cluster), then the machine learning system may provide a first recommendation. Additionally, or alternatively, the machine learning system may perform a first automated action and/or may cause a first automated action to be performed (e.g., by instructing another device to perform the automated action) based on classifying the new observation in the first cluster.

As another example, if the machine learning system were to classify the new observation in a second cluster (e.g., a low confidence score cluster), then the machine learning system may provide a second (e.g., different) recommendation and/or may perform or cause performance of a second (e.g., different) automated action.

In some implementations, the recommendation and/or the automated action associated with the new observation may be based on a target variable value having a particular label (e.g., classification or categorization), may be based on whether a target variable value satisfies one or more threshold (e.g., whether the target variable value is greater than a threshold, is less than a threshold, is equal to a threshold, falls within a range of threshold values, or the like), and/or may be based on a cluster in which the new observation is classified.

In this way, the machine learning system may apply a rigorous and automated process to identifying and verifying a medication. The machine learning system enables recognition and/or identification of tens, hundreds, thousands, or millions of features and/or feature values for tens, hundreds, thousands, or millions of observations, thereby increasing accuracy and consistency and reducing delay associated with identifying and verifying a medication relative to requiring computing resources to be allocated for tens, hundreds, or thousands of operators to manually identify and verify a medication using the features or feature values.

As indicated above, FIG. 3 is provided as an example. Other examples may differ from what is described in connection with FIG. 3.

Figure 4:
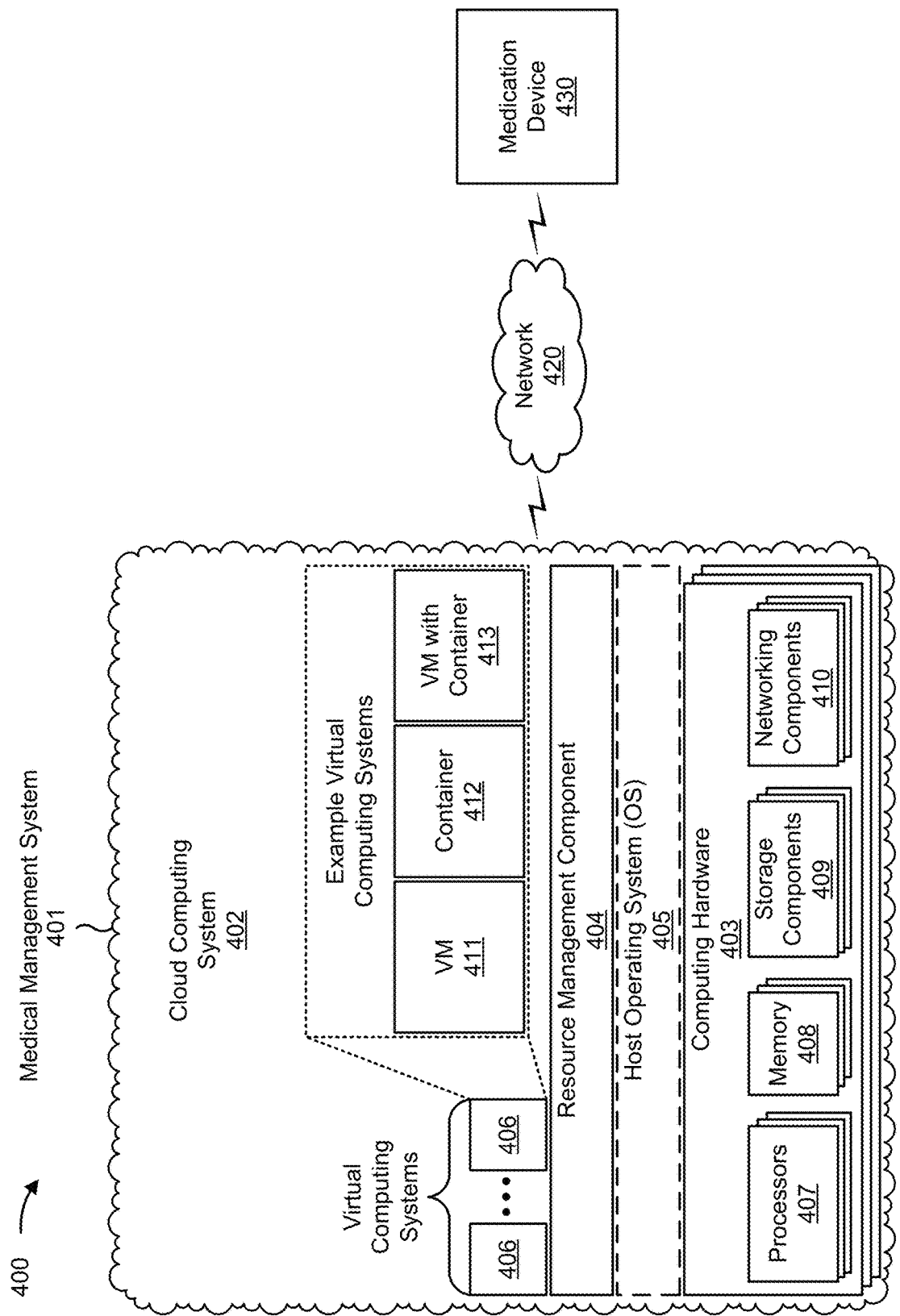
FIG. 4 is a diagram of an example environment in which systems and/or methods described herein may be implemented.

FIG. 4 is a diagram of an example environment 400 in which systems and/or methods described herein may be implemented. As shown in FIG. 4, environment 400 may include a medical management system 401, which may include one or more elements of and/or may execute within a cloud computing system 402. The cloud computing system 402 may include one or more elements 403-413, as described in more detail below. As further shown in FIG. 4, environment 400 may include a network 420 and a medication device 430. Devices and/or elements of environment 400 may interconnect via wired connections and/or wireless connections.

The cloud computing system 402 includes computing hardware 403, a resource management component 404, a host operating system (OS) 405, and/or one or more virtual computing systems 406. The resource management component 404 may perform virtualization (e.g., abstraction) of computing hardware 403 to create the one or more virtual computing systems 406. Using virtualization, the resource management component 404 enables a single computing device (e.g., a computer, a server, and/or the like) to operate like multiple computing devices, such as by creating multiple isolated virtual computing systems 406 from computing hardware 403 of the single computing device. In this way, computing hardware 403 can operate more efficiently, with lower power consumption, higher reliability, higher availability, higher utilization, greater flexibility, and lower cost than using separate computing devices.

Computing hardware 403 includes hardware and corresponding resources from one or more computing devices. For example, computing hardware 403 may include hardware from a single computing device (e.g., a single server) or from multiple computing devices (e.g., multiple servers), such as multiple computing devices in one or more data centers. As shown, computing hardware 403 may include one or more processors 407, one or more memories 408, one or more storage components 409, and/or one or more networking components 410. Examples of a processor, a memory, a storage component, and a networking component (e.g., a communication component) are described elsewhere herein.

The resource management component 404 includes a virtualization application (e.g., executing on hardware, such as computing hardware 403) capable of virtualizing computing hardware 403 to start, stop, and/or manage one or more virtual computing systems 406. For example, the resource management component 404 may include a hypervisor (e.g., a bare-metal or Type 1 hypervisor, a hosted or Type 2 hypervisor, and/or the like) or a virtual machine monitor, such as when the virtual computing systems 406 are virtual machines 411. Additionally, or alternatively, the resource management component 404 may include a container manager, such as when the virtual computing systems 406 are containers 412. In some implementations, the resource management component 404 executes within and/or in coordination with a host operating system 405.

A virtual computing system 406 includes a virtual environment that enables cloud-based execution of operations and/or processes described herein using computing hardware 403. As shown, a virtual computing system 406 may include a virtual machine 411, a container 412, a hybrid environment 413 that includes a virtual machine and a container, and/or the like. A virtual computing system 406 may execute one or more applications using a file system that includes binary files, software libraries, and/or other resources required to execute applications on a guest operating system (e.g., within the virtual computing system 406) or the host operating system 405.

Although the medical management system 401 may include one or more elements 403-413 of the cloud computing system 402, may execute within the cloud computing system 402, and/or may be hosted within the cloud computing system 402, in some implementations, the medical management system 401 may not be cloud-based (e.g., may be implemented outside of a cloud computing system) or may be partially cloud-based. For example, the medical management system 401 may include one or more devices that are not part of the cloud computing system 402, such as device 500 of FIG. 5, which may include a standalone server or another type of computing device. The medical management system 401 may perform one or more operations and/or processes described in more detail elsewhere herein.

Network 420 includes one or more wired and/or wireless networks. For example, network 420 may include a cellular network, a public land mobile network (PLMN), a local area network (LAN), a wide area network (WAN), a private network, the Internet, and/or the like, and/or a combination of these or other types of networks. The network 420 enables communication among the devices of environment 400.

Medication device 430 includes one or more devices capable of receiving, generating, storing, processing, and/or providing information, such as information described herein. For example, medication device 430 may include a computer (e.g., a desktop computer, a laptop computer, a tablet computer, a handheld computer, a server device, etc.), a mobile phone (e.g., a smart phone, a radiotelephone, etc.), an internet of things (IoT) device or smart appliance, or a similar device. In some implementations, medication device 430 may include one or more components, such as one or more receptacles to hold a container filled with medication, one or more camera devices to obtain image data relating to the medication and/or a seal of the container, one or more receptacle window to facilitate the one or more camera devices to obtain the image data, one or more weighing devices to obtain weight data relating to the medication, and/or the like. In some implementations, medication device 430 may receive information from and/or transmit information to medication management system 401 and/or the like.

The number and arrangement of devices and networks shown in FIG. 4 are provided as an example. In practice, there may be additional devices and/or networks, fewer devices and/or networks, different devices and/or networks, or differently arranged devices and/or networks than those shown in FIG. 4. Furthermore, two or more devices shown in FIG. 4 may be implemented within a single device, or a single device shown in FIG. 4 may be implemented as multiple, distributed devices. Additionally, or alternatively, a set of devices (e.g., one or more devices) of environment 400 may perform one or more functions described as being performed by another set of devices of environment 400.

Figure 5:
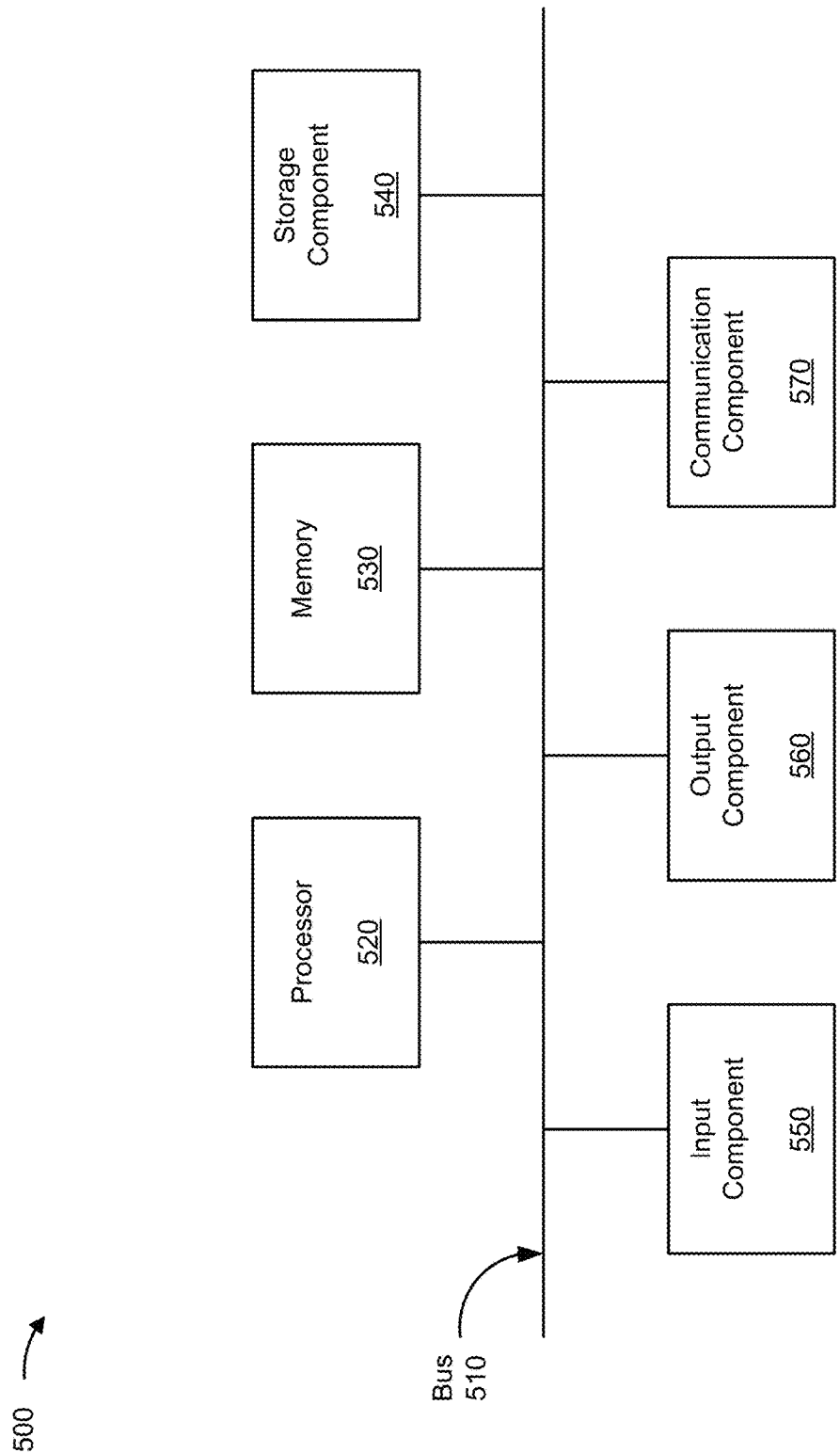
FIG. 5 is a diagram of example components of one or more devices of FIG. 4.

FIG. 5 is a diagram of example components of a device 500, which may correspond to medication management system 401 and/or medication device 430. In some implementations, medication management system 401 and/or medication device 430 may include one or more devices 500 and/or one or more components of device 500. As shown in FIG. 5, device 500 may include a bus 510, a processor 520, a memory 530, a storage component 540, an input component 550, an output component 560, and a communication component 570.

Bus 510 includes a component that enables wired and/or wireless communication among the components of device 500. Processor 520 includes a central processing unit, a graphics processing unit, a microprocessor, a controller, a microcontroller, a digital signal processor, a field-programmable gate array, an application-specific integrated circuit, and/or another type of processing component. Processor 520 is implemented in hardware, firmware, or a combination of hardware and software. In some implementations, processor 520 includes one or more processors capable of being programmed to perform a function. Memory 530 includes a random access memory, a read only memory, and/or another type of memory (e.g., a flash memory, a magnetic memory, and/or an optical memory).

Storage component 540 stores information and/or software related to the operation of device 500. For example, storage component 540 may include a hard disk drive, a magnetic disk drive, an optical disk drive, a solid state disk drive, a compact disc, a digital versatile disc, and/or another type of non-transitory computer-readable medium. Input component 550 enables device 500 to receive input, such as user input and/or sensed inputs. For example, input component 550 may include a touch screen, a keyboard, a keypad, a mouse, a button, a microphone, a switch, a sensor, a global positioning system component, an accelerometer, a gyroscope, and/or an actuator. Output component 560 enables device 500 to provide output, such as via a display, a speaker, and/or one or more light-emitting diodes. Communication component 570 enables device 500 to communicate with other devices, such as via a wired connection and/or a wireless connection. For example, communication component 570 may include a receiver, a transmitter, a transceiver, a modem, a network interface card, and/or an antenna.

Device 500 may perform one or more processes described herein. For example, a non-transitory computer-readable medium (e.g., memory 530 and/or storage component 540) may store a set of instructions (e.g., one or more instructions, code, software code, and/or program code) for execution by processor 520. Processor 520 may execute the set of instructions to perform one or more processes described herein. In some implementations, execution of the set of instructions, by one or more processors 520, causes the one or more processors 520 and/or the device 500 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 5 are provided as an example. Device 500 may include additional components, fewer components, different components, or differently arranged components than those shown in FIG. 5. Additionally, or alternatively, a set of components (e.g., one or more components) of device 500 may perform one or more functions described as being performed by another set of components of device 500.

Figure 6:
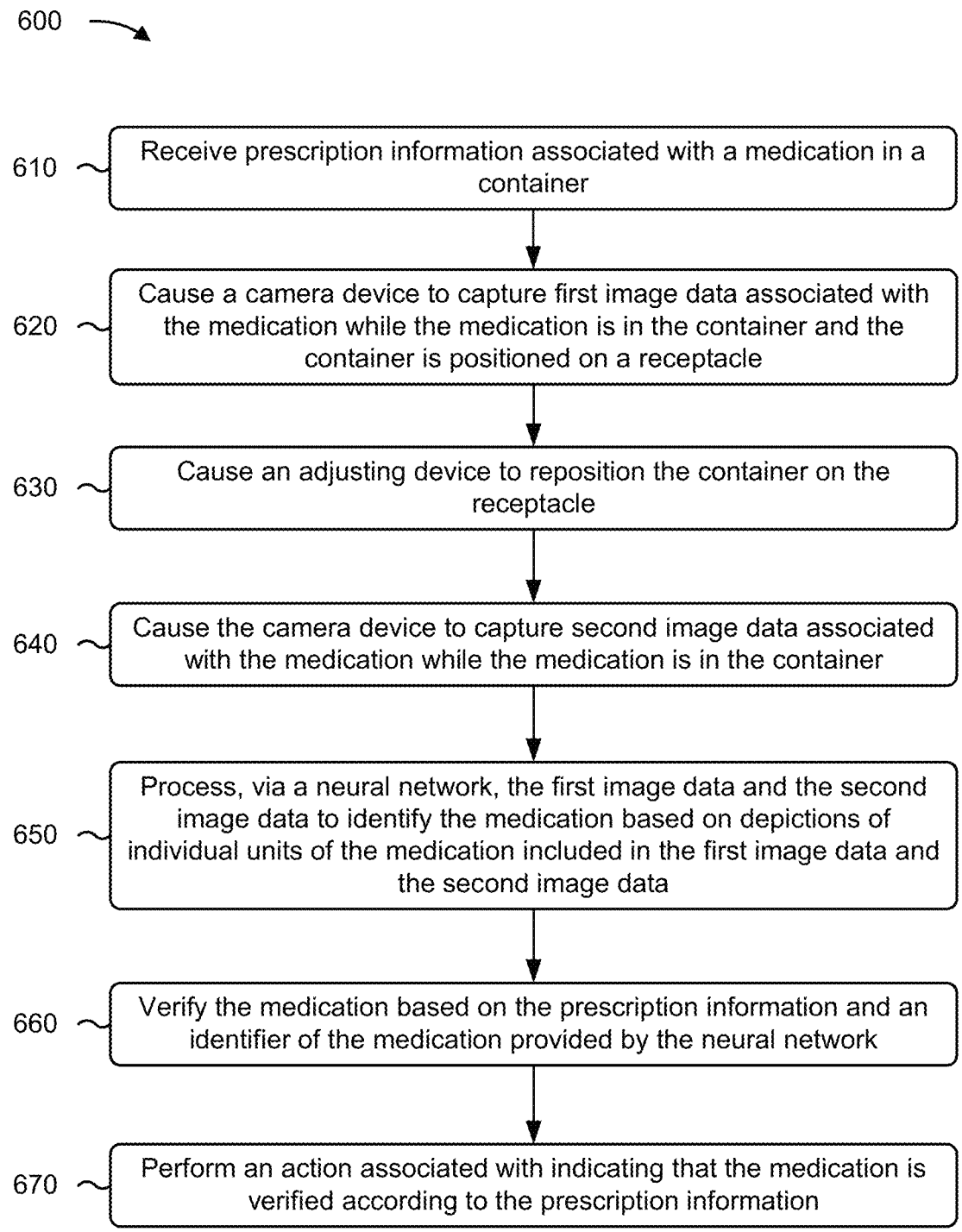
FIG. 6 is a flowchart of an example process relating to identification and verification of medication.

FIG. 6 is a flowchart of an example process 600 associated with identification and verification of medication. In some implementations, one or more process blocks of FIG. 6 may be performed by a device (e.g., medication management system 401). In some implementations, one or more process blocks of FIG. 6 may be performed by another device or a group of devices separate from or including the device, such as medication device 430. Additionally, or alternatively, one or more process blocks of FIG. 6 may be performed by one or more components of device 500, such as processor 520, memory 530, storage component 540, input component 550, output component 560, and/or communication component 570.

As shown in FIG. 6, process 600 may include receiving prescription information associated with a medication in a container (block 610). For example, the device may receive prescription information associated with a medication in a container, as described above. The prescription information may include an identifier of the medication, information identifying a dosage of the medication, and/or information identifying an amount of the medication. The information identifying the amount of the medication may include information identifying a quantity of the medication in the container, a weight of a unit (e.g., a pill, a capsule, a tablet, and/or the like) of the medication, a total weight of the medication not including a weight of the container, a total weight of the medication including the weight of the container, and/or the like.

As further shown in FIG. 6, process 600 may include causing a camera device to capture first image data associated with the medication while the medication is in the container and the container is positioned on a receptacle (block 620). For example, the device may cause a camera device to capture first image data associated with the medication while the medication is in the container and the container is positioned on a receptacle, as described above. The receptacle may include a receptacle window that is configured to support the container while the camera device captures the image data. The camera device may be positioned under the receptacle window and the receptacle window may be within a field of view of the camera device.

As further shown in FIG. 6, process 600 may include causing an adjusting device to reposition the container on the receptacle (block 630). For example, the device may cause an adjusting device to reposition the container on the receptacle, as described above. In some implementations, the adjusting device comprises a vibration mechanism that is configured to move the container on the receptacle.

As further shown in FIG. 6, process 600 may include causing the camera device to capture second image data associated with the medication while the medication is in the container (block 640). For example, the device may cause the camera device to capture second image data associated with the medication while the medication is in the container, as described above. In some implementations, prior to causing the camera device to capture the second image data, the device may adjust a polarization of a lens of the camera device, a light filter of a lens of the camera device, a zoom setting of the camera device, and/or a wavelength of a light emitter associated with the camera device. For example, the device may include a polarized lens configured to reduce reflected light depicted in images associated with the image data, a light filter configured to filter a particular wavelength of light from images associated with the image data, a lens configured to adjust dimensions of the field of view, and/or a light emitter configured to adjust a characteristic of light in images associated with the image data. Alternatively, and/or additionally, the receptacle window may include one or more adjustable filters. Prior to causing the camera device to capture the second image data, the device may adjust the polarized lens, the light filter, the lens, the light emitter, and/or the one or more adjustable filters.

In some implementations, the device may cause the camera device to capture a plurality of second image data corresponding to a plurality of images associated with the medication while the medication is in the container. The device may iteratively process images, of the plurality of images, after corresponding second image data is captured by the camera device. The images of the plurality of images may be obtained until the medication is identified in an image of the plurality of images and/or until a predetermined quantity of the plurality of images are obtained. The predetermined quantity may be associated with a configuration of the neural network.

As further shown in FIG. 6, process 600 may include processing, via a neural network, the first image data and the second image data to identify the medication based on depictions of individual units of the medication included in the first image data and the second image data (block 650). For example, the device may process, via a neural network, the first image data and the second image data to identify the medication based on depictions of individual units of the medication included in the first image data and the second image data, as described above. The neural network may comprise a convolutional neural network that is configured to segment the first image data and the second image data into the depictions of the individual units, determine classification scores of the depictions that are associated with identifying the medication based on corresponding ones of the individual units, and/or identify the medication based on the classification scores.

As further shown in FIG. 6, process 600 may include verifying the medication based on the prescription information and an identifier of the medication provided by the neural network (block 660). For example, the device may verify the medication based on the prescription information and an identifier of the medication provided by the neural network, as described above. In some implementations, the device causes a weighing device to obtain weight data associated with the medication while the medication is within the container. The device may verify the medication based on the prescription information, the identifier, and the weight data.

As further shown in FIG. 6, process 600 may include performing an action associated with indicating that the medication is verified according to the prescription information (block 670). For example, the device may perform an action associated with indicating that the medication is verified according to the prescription information, as described above. In some implementations, performing the action may include the device indicating, via a display, that the medication is verified and/or providing, to a medication management system, a notification that the medication is verified in association with the prescription information.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   receiving, by a device, prescription information associated with a medication in a container;
   causing, by the device, a camera device to capture first image data associated with the medication while the medication is in the container and the container is positioned on a receptacle;
   causing, by the device, an adjusting device to reposition the container on the receptacle;
   causing, by the device, the camera device to capture second image data associated with the medication while the medication is in the container;
   processing, by the device and via a neural network, the first image data and the second image data to identify the medication based on depictions of individual units of the medication included in the first image data and the second image data,
      wherein the neural network is configured to:
         segment the first image data and the second image data into the depictions of the individual units,
         determine one or more classification scores of one or more of the depictions of the individual units, and
         provide, based on the one or more classification scores, an identifier of the medication; and
   verifying, by the device, the medication based on the prescription information and the identifier of the medication provided by the neural network.

2. The method of claim 1, wherein the prescription information includes at least one of:
   the identifier of the medication;
   information identifying a dosage of the medication; or
   information identifying an amount of the medication.

3. The method of claim 1, wherein the adjusting device comprises a vibration mechanism that is configured to move the container on the receptacle.

4. The method of claim 1, further comprising:
   causing a weighing device to obtain weight data associated with the medication while the medication is within the container,
      wherein the medication is verified based on the prescription information, the identifier, and the weight data.

5. The method of claim 1, further comprising:
   prior to causing the camera device to capture the second image data, adjusting at least one of:
      a polarization of a lens of the camera device;
      a light filter of the lens of the camera device;
      a zoom setting of the camera device; or
      a wavelength of a light emitter associated with the camera device.

6. The method of claim 1, further comprising:
   indicating, via a display, that the medication is verified; or
   providing, to a medication management system, a notification that the medication is verified in association with the prescription information.

7. A device, comprising:
   one or more memories; and
   one or more processors, communicatively coupled to the one or more memories, configured to:
      receive prescription information associated with a medication in a container,
         wherein the container is positioned on a receptacle of the device;
      obtain a plurality of images of the medication by iteratively:
         adjusting, via an adjusting device, the container on the receptacle to attempt to reposition individual units of the medication within container, and
         capturing, via a camera device, image data associated with the medication while the medication is in the container;
      process, via a neural network, the plurality of images to identify the medication based on one or more depictions of a unit of the individual units,
         wherein the neural network is configured to:
            segment one or more of the plurality of images into the one or more depictions of the unit of the individual units,
            determine one or more classification scores of the one or more depictions of the unit of the individual units, and
            provide an output based on the one or more classification scores; and
      verify the medication based on the prescription information and the output provided by the neural network.

8. The device of claim 7,
   wherein the output includes an identifier of the medication, and
   wherein the prescription information includes at least one of:
      the identifier of the medication;
      information identifying a dose of the medication; or
      information identifying an amount of the medication.

9. The device of claim 7, wherein the receptacle includes a receptacle window that is configured to support the container while the camera device captures the image data,
   wherein the camera device is positioned under the receptacle window and the receptacle window is within a field of view of the camera device.

10. The device of claim 7, wherein images of the plurality of images are iteratively processed after corresponding image data is captured via the camera device,
    wherein the images of the plurality of images are obtained until at least one of:
       the medication is identified in an image of the plurality of images, or
       a predetermined quantity of the plurality of images are obtained.

11. The device of claim 7, wherein images of the plurality of images are iteratively obtained until a predetermined quantity of the plurality of images are obtained,
    wherein the predetermined quantity is associated with a configuration of the neural network.

12. The device of claim 7, wherein the one or more processors are further configured to:
    indicate, via a display, that the medication is verified; or
    provide, to a medication management system, a notification that the medication is verified in association with the prescription information.

13. The device of claim 7, wherein the neural network comprises a convolutional neural network.

14. The device of claim 7, wherein the one or more processors are further configured to:
adjust one or more of a polarization of a lens of the camera device to reduce reflected light, a light filter of the lens of the camera device to filter a particular wavelength of light, or a wavelength of a light emitter associated with the camera device to adjust a color of light.

15. A medication analysis system comprising:
a receptacle that is configured to support a container on a receptacle window;
a camera device positioned beneath the receptacle window and configured to have the receptacle window within a field of view of the camera device;
an adjusting device configured to move the receptacle to adjust a position of a medication in the container; and
a control device configured to:
cause the adjusting device to reposition the container on the receptacle,
cause the camera device to capture image data associated with the medication, and
process, via a neural network, the image data to identify the medication,
wherein the neural network is configured to:
segment the image data into one or more depictions of one or more individual units of the medication;
determine one or more classification scores of the one or more depictions of the one or more individual units of the medication; and
provide an output for the medication based on the one or more classification scores, and
verify the medication based on the output provided by the neural network.

16. The medication analysis system of claim 15, wherein the receptacle window includes one or more adjustable filters.

17. The medication analysis system of claim 15, wherein the adjusting device comprises a vibration mechanism that is configured to move the container on the receptacle.

18. The medication analysis system of claim 15, further comprising at least one of:
a polarized lens configured to reduce reflected light depicted in images associated with the image data;
a light filter configured to filter a particular wavelength of light from images associated with the image data;
a lens configured to adjust dimensions of the field of view; or
a light emitter configured to adjust a characteristic of light in images associated with the image data.

19. The medication analysis system of claim 15, wherein the control device, when verifying the medication, is configured to:
obtain prescription information associated with the medication; and
verify the medication based on the prescription information and the output provided by the neural network.

20. The medication analysis system of claim 19, further comprising:
a weighing device associated with the receptacle that is configured to obtain weight data associated with the medication,
wherein the control device is further configured to:
cause the weighing device to obtain the weight data associated with the medication while the medication is within the container,
wherein the medication is verified based on the prescription information, the output provided by the neural network, and the weight data.

* * * * *